(12) United States Patent
Moszner

(10) Patent No.: US 9,084,589 B2
(45) Date of Patent: Jul. 21, 2015

(54) METHOD OF PRODUCING A MEDICAL IMPLANTABLE DEVICE AND MEDICAL IMPLANTABLE DEVICE

(75) Inventor: Robert Moszner, Bad Klosterlausnitz (DE)

(73) Assignee: Occlutech Holding AG, Schaffhausen (CH)

( * ) Notice: Subject to any disclaimer, the term of this patent is extended or adjusted under 35 U.S.C. 154(b) by 1236 days.

(21) Appl. No.: 12/671,884

(22) PCT Filed: Aug. 4, 2008

(86) PCT No.: PCT/EP2008/060248
§ 371 (c)(1),
(2), (4) Date: Aug. 16, 2011

(87) PCT Pub. No.: WO2009/016265
PCT Pub. Date: Feb. 5, 2009

(65) Prior Publication Data
US 2011/0295298 A1    Dec. 1, 2011

Related U.S. Application Data

(60) Provisional application No. 60/953,649, filed on Aug. 2, 2007, provisional application No. 60/970,200, filed on Sep. 5, 2007.

(30) Foreign Application Priority Data

Jul. 17, 2008   (EP) ..................... 08160672

(51) Int. Cl.
*A61M 29/00*   (2006.01)
*A61B 17/00*   (2006.01)
*A61B 17/12*   (2006.01)
*A61F 2/01*    (2006.01)

(Continued)

(52) U.S. Cl.
CPC ....... *A61B 17/0057* (2013.01); *A61B 17/12022* (2013.01); *A61B 17/12109* (2013.01); *A61B 17/12113* (2013.01); *A61B 17/12172* (2013.01); *A61F 2/01* (2013.01); *A61F 2/90* (2013.01); *A61F 2002/30092* (2013.01); *A61F 2210/0014* (2013.01); *A61F 2240/001* (2013.01)

(58) Field of Classification Search
USPC ................. 606/191–199, 200, 213, 214, 215; 623/1.11; 228/170
See application file for complete search history.

(56) References Cited

U.S. PATENT DOCUMENTS

| 5,683,411 A | 11/1997 | Kavteladze et al. |
| 5,725,552 A | 3/1998 | Kotula et al. |
| 5,944,738 A | 8/1999 | Amplatz et al. |

(Continued)

FOREIGN PATENT DOCUMENTS

| CN | 2524710 Y | 12/2002 |
| CN | 2613248 Y | 4/2004 |

(Continued)

*Primary Examiner* — Katrina Stransky
(74) *Attorney, Agent, or Firm* — Inskeep IP Group, Inc.

(57) ABSTRACT

A method for producing a connection between two components of a medical implant which preferably are composed of different materials which cannot be welded to one another is described. Furthermore, a medical implant which is produced according to the method is described. Moreover, the medical implant comprises an connection interface whereon said medical implant is detachable from an introduction wire or introduction implement.

15 Claims, 16 Drawing Sheets

(51) Int. Cl.
*A61F 2/90* (2013.01)
*A61F 2/30* (2006.01)

(56) References Cited

U.S. PATENT DOCUMENTS

| | | |
|---|---|---|
| 6,168,622 B1 | 1/2001 | Mazzocchi |
| 6,174,322 B1 | 1/2001 | Schneidt |
| 6,214,029 B1 | 4/2001 | Thill et al. |
| 6,506,204 B2 | 1/2003 | Mazzocchi |
| 6,792,979 B2 | 9/2004 | Konya et al. |
| 6,797,083 B2 | 9/2004 | Peterson |
| 2005/0004652 A1 | 1/2005 | van der Burg et al. |
| 2006/0224183 A1 | 10/2006 | Freudenthal |
| 2007/0043391 A1 | 2/2007 | Moszner et al. |
| 2007/0167980 A1* | 7/2007 | Figulla et al. ............... 606/213 |
| 2010/0004679 A1* | 1/2010 | Osypka ........................ 606/213 |

FOREIGN PATENT DOCUMENTS

| | | |
|---|---|---|
| CN | 1736346 A | 2/2006 |
| DE | 102006013770 A1 | 9/2007 |
| DE | 102006045545 A1 * | 4/2008 |
| EP | 0 719 522 A1 | 7/1996 |
| EP | 1 576 929 A2 | 9/2005 |
| WO | WO 96/01599 A1 | 1/1996 |
| WO | WO 98/47430 A1 | 10/1998 |
| WO | WO 99/12478 A1 | 3/1999 |
| WO | WO 02/071977 A2 | 9/2002 |
| WO | WO 2004/064671 A2 | 8/2004 |
| WO | WO 2005/020822 A1 | 3/2005 |
| WO | WO 2005/099365 A2 | 10/2005 |
| WO | WO 2007/140797 A1 | 12/2007 |
| WO | WO 2008037322 A1 * | 4/2008 |

* cited by examiner

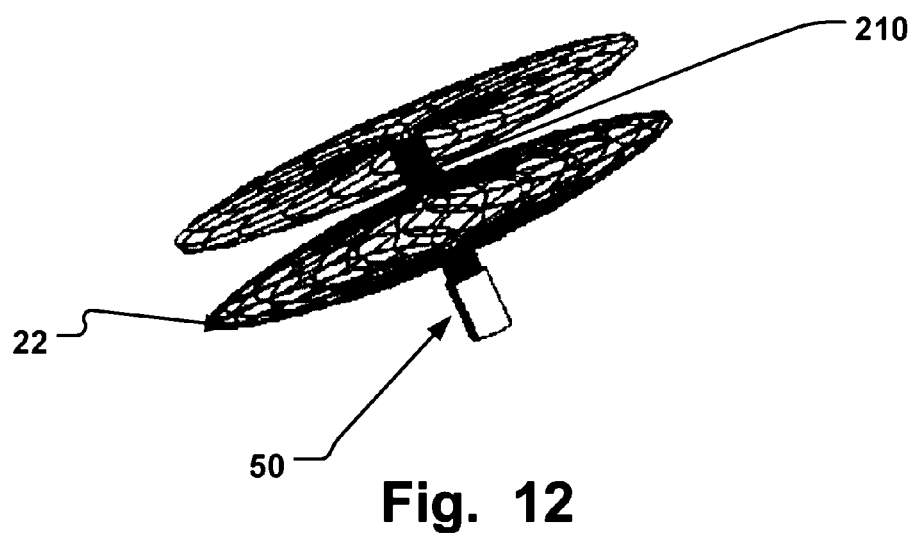
Fig. 12
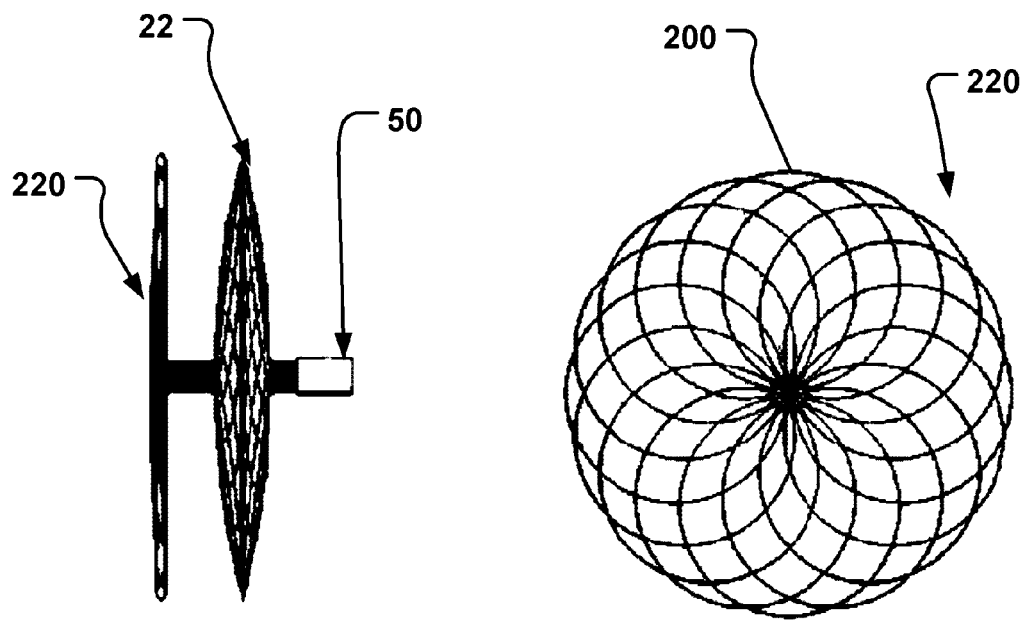
Fig. 13
Fig. 14

METHOD OF PRODUCING A MEDICAL IMPLANTABLE DEVICE AND MEDICAL IMPLANTABLE DEVICE

RELATED APPLICATIONS

This application claims priority to International Patent Application No. PCT/EP2008/060248, International Filing Date 4 Aug. 2008, entitled Method Of Producing A Medical Implantable Device And Medical Implantable Device, which in turn claims priority to U.S. Provisional Application Ser. No. 60/953,649 filed Aug. 2, 2007; U.S. Provisional Application Ser. No. 60/970,200 filed Sep. 5, 2007; and European Application Serial No. 08160672.5 filed Jul. 17, 2008, all of which are hereby incorporated herein by reference.

FIELD OF THE INVENTION

The present invention pertains, in general terms, to medical implants and methods for producing these. The present invention relates, more particular, to a production method for a medical implant and a medical implantable device, such as a collapsible device, including a septal or vascular occlusion device, a stent, or an aneurysm treatment device. The medical implant comprises, at least during manufacturing thereof, a bundle of strands or wires, to which bundle a connection of another element, such as a delivery connection adapter, is desired to be carried out.

BACKGROUND OF THE INVENTION

Medical implants often comprise two components which are difficult to reliably connect to one another at reasonable cost. For example, elements made of NiTinol (metal alloy of nickel and titanium) may only be machined with difficulty. NiTinol workpieces may for example extremely difficult be provided with bores or threads. This applies particularly to components which have bundles of strands. Moreover, elements made of NiTinol cannot be connected to elements made of other metals virtually at all by soldering or welding, since such connections are at least not permanently durable and therefore do not satisfy the requirements to be fulfilled by medical implants. Such connections can therefore be implemented only with difficulty.

One possibility is to push a clamp over a bundle of strands and clamp this clamp together with the bundle of strands, as is known, for example, in the case of cable ends.

However, such clamping of a per se flexible bundle of wires or strands may not reliably provide long-term fixation of the clamp to the bundle. The clamp may loosen. The clamp may also affect the strands and affect strength of the strands' material.

Clamps for clamping bundles of strands of a tubular braided metal fabric at two ends of a medical device is disclosed in WO99/12478. The bundles are prevented from unraveling by means of one clamp at each end of the device. Each clamp is clamping together a distal and a proximal bundle of strands of the tubular fabric. The clamps are clamped to the bundle after cutting of the latter to a desired length. One of the clamps comprises an internal thread for attachment of the device to a guidewire during delivery. Clamping of a tubular fabric, in particular a braided tubular fabric, may prove difficult to achieve before the fabric unravels.

Alternatively, it is disclosed in WO99/12478 that the ends may be welded. However, by welding the ends together, it becomes difficult to attach a delivery device to one of the ends as welded clots of strands are not directly provideable with a thread. Welded ends tend to also to be irregular in shape as the liquefied metal strands flow away before cooling down and becoming solidified again. This affects quality of the manufacturing process contrary to the high quality requirements of medical devices.

Moreover, the type of clamped connection disclosed in WO99/12478 is also not permanently reliable, as explained above. For example when the medical implant is constantly exposed to loads and deformations in the body, such as, for example, in the heart, structural weaknesses may occur due to the clamp.

Hence, a reliable permanent connection of an element to a bundle of strands is needed.

Similar issues apply when connection of the bundle to other elements is to be made in a reliable way for temporary connections, e.g. during delivery of the medical implant.

Another issue is reduction of cost of manufacture of such medical implants having permanent or temporary connections of bundles to other elements. For instance it is desired to minimize manual handling steps.

The connection of the elements may be temporary or permanently arranged. Positive or non-positive connection of the elements to the bundle of strands is facilitated. The different elements affixed to each other may be made of different materials that are not weldable to one another.

SUMMARY OF THE INVENTION

The object of the invention is, for example, to overcome the abovementioned disadvantages of the conventional devices and connection methods for various elements of medical implants and to specify a reliable and/or patient-friendly/safe solution.

The above mentioned object is achieved in that the device is manufactured according to a method, which has acquired the features of appended Claim 1, according to a first aspect of the invention.

The method is a method for producing a fixed or releasable positive or non-positive connection between two components. A connection interface is provided facilitating fixed or releasable connection of the two components.

The method is a method of producing a medical implantable device comprising a bundle of strands, the method comprising holding the bundle of strands of the medical implantable device in a desired shape with a holding unit, and subsequently cutting the bundle of wires while holding the bundle within the holding unit, thus creating a cut end of the bundle of wires, and subsequently welding the bundle of strands together at the cut end while keeping the holding unit arranged at the cut end, thereby creating a welded end of the bundle of strands having defined proportions and dimensions given at least partly by the holding unit, thereby providing a connection interface at the welded end devised for fastening an external element to the welded end.

According to a second aspect of the invention, a medical implantable device is provided.

More particular, wire ends are fixated in a bundle of defined shape, thus providing a well defined connection interface devised for fastening an external element, e.g. a delivery adapter, such as a steel sleeve.

Visibility in X-ray may be improved by attaching components with different radiopacity to each other as described herein.

The medical implantable device comprises a bundle of strands, the bundle of strands of the device comprises a welded end having a welded end portion, wherein the welded end portion has defined proportions and dimensions configured as a connection interface, and an external element fastened at the welded end to the connection interface in a non-clamped manner.

In an embodiment the medical implantable device is produced by the method according to the first aspect of the invention.

Further embodiments of the invention are defined in the dependent claims, wherein features for the second and subsequent aspects of the invention are as for the first aspect mutatis mutandis.

BRIEF DESCRIPTION OF THE DRAWINGS

The invention will be explained in more detail below with reference to an exemplary embodiment illustrated in the drawings, reference being made to the accompanying drawings in which:

FIGS. 12 to 14 show several examples of occlusion devices having proximal bundle ends produced according to embodiments of the method of the invention.

DETAILED DESCRIPTION OF AN EMBODIMENT

Figure 1:
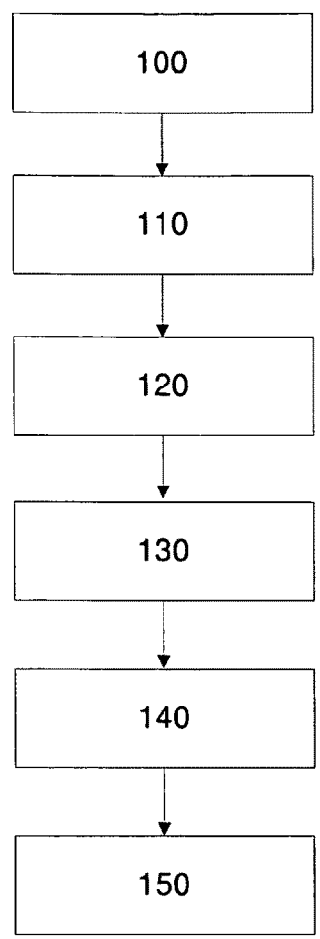
FIG. 1 shows a schematic flowchart of an embodiment of a production method.

According to an embodiment, the medical implant is an occluder. An occlusion instrument of this type is at least partially known in principle from medical technology. However, these known devices do not have specifically advantageous produced ends of wire bundles, as the invention provides.

For example, an occlusion instrument for the treatment of septum defects is generally known from DE 10 338 702 of 22nd Aug. 2003, which is incorporated by reference in its entirety for all purposes. The occlusion instrument comprises a mesh of thin wires or threads. It acquires a suitable shape by means of a forming and heat treatment method. The known occlusion instrument has a distal retention region which is shaped particularly flat, a proximal retention region and a cylindrical web between the proximal and the distal retention region. At the proximal retention region, the ends of the wires forming the mesh converge in a hub. In this case, there is provision for the two retention regions of the known occlusion instrument to come to bear in a septum, on both sides of a shunt to be closed, as a result of a mostly intravascular intervention, while the web runs through the shunt.

Similar instruments are described in the patent application Germany number 102005053957.2 of 11 May 2005 and the equivalent applications PCT/EP2005/012130 of 11 May 2005 and US application US11/271,751 of 19 December 2005, all of the same applicant as the present application, which herein are incorporated herein by reference in their entirety for all purposes.

Other medical implants are e.g. PDA plugs, stents, LAA occluders, Aneurysm filling implants, intravascular filters, intravascular occluders, intraluminal occluders, etc.

For instance a vascular occlusion device is shown in EP 0808 138. The device is adapted so as to permanently close an orifice with a dynamic blood flow and, for this purpose, has a special design and is not suitable for heart occlusions. It has a bundle of strands at each opposite end, which ends need to be clamped in order to prevent unraveling of the device.

Embodiments of the production method comprise a series of "laser and plasma welding" machining operations in order to connect the bundle of wires to an external element. For instance the external element is a high-grade steel element that is connected to a bundle wires. The steel element is for instance a high-grade steel, threaded delivery coupling. When the wires are made of a nickel titanium alloy, such as NiTinol, the steel adapter is not attachable to the bundle by welding.

In embodiments a sleeve is arranged around a wire bundle to be a holder, but not adapted to clamp. It is pointed out that a holder is merely arranged around one or more items it holds therein. In contrast a clamp may be a specific holder which has given dimensions to radially compress elements therein, i.e. to clamp the items.

A detailed description for producing a joining connection is described below.

Welding of two elements to each other is avoided while a reliable connection is provided. This is made both in a repeatable manner and at potentially reduced production cost of the medical implant. Mass production is in particular facilitated while providing reliable high quality products.

In order to ensure that the occlusion instrument can be implanted, it is required to be releasably attached during delivery to an implantation site to an introduction implement or device, and e.g. an introduction wire, pusher, etc. There is provision for the end of the medical device having a bundle of strands to have an element which can be brought into engagement with the introduction implement and/or wire. The bundle may be arranged at a retention region of the medical device, such as an end of a closed dumbbell, hourglass, pear, bell, or similar shape. The connection must reliably withstand the forces for drawing into the catheter sheath of the introduction implement and during forward or backward movements in the catheter sheath. In addition, rotational transmission of torque may be desired during delivery for positioning the medical implant correctly and smoothly in the body.

The connection of an intermediate element to the bundle may be temporary during insertion, or permanent. In a permanent connection only the introduction element, such as an introduction wire, is connected to the medical device during delivery. The intermediate element is permanently connected to the bundle.

The intermediate element is e.g. a coupling that is preferably equipped with an internal thread as a counterpiece to "screw introduction wires" found on the market. However, other couplings are envisioned, e.g. bayonet style couplings. Gripping couplings may be alternative couplings.

After the catheter sheath has been left and the implant has been placed in the heart, the screw wire can be uncoupled by rotation in the case of threaded coupling, but, before uncoupling, affords the possibility of recovering the occluder in the event of possible mispositions. Further release methods could be to un-lock the implant by means of a release intersection between the implant and the catheter similar to a bayonet fitting.

Process Description

An embodiment of the method is illustrated with the aid of the steps according to FIG. 1 and is explained further below.

Figure 2A:
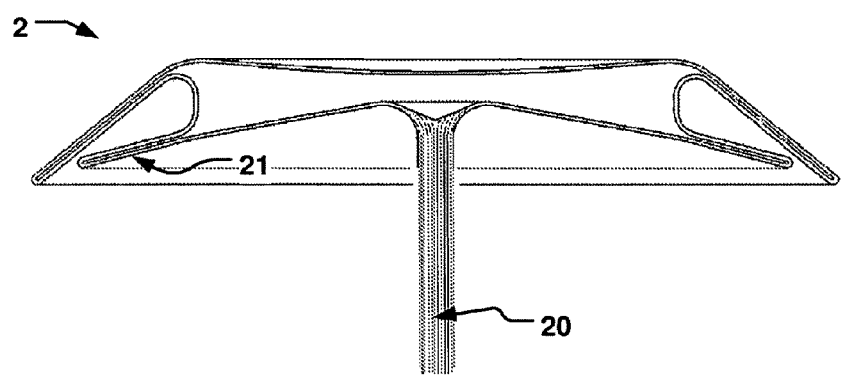
FIGS. 2a, 2b and 2c show a schematic sectional illustration of an occlusion instrument with axially aligned wire ends.
Figure 2B:
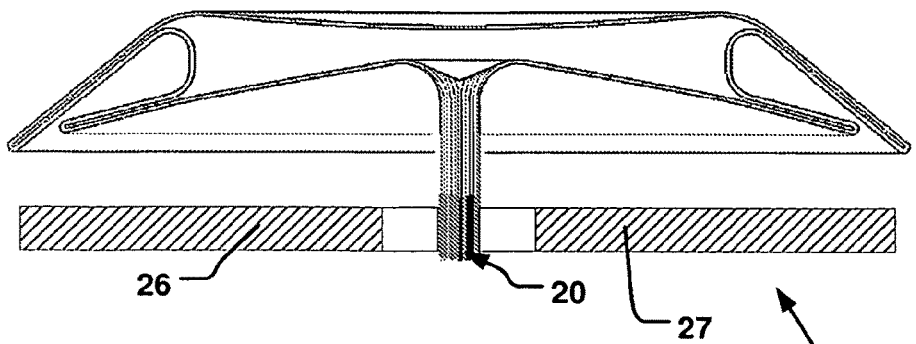

After the completion of the occluder fabric blank, as shown, for example, in FIG. 2a or FIG. 2b, a bundle of wires 20 that is proximally projecting, and which is approximately axially aligned by a suitable shaping as a result of a thermal effect, is cut off, by means of a laser beam. A defined proximal end portion of the wire bundle is then welded or fused. During cutting and welding, the bundle is hold by a holding unit. The holding unit is e.g. a sleeve or a jig template arranged around the bundle. The sleeve may be a sleeve of the same material as the bundle, e.g. NiTinol. The bundle is attached to the NiTinol sleeve by means of microplasma welding. The parallel orientation of the ends as well as this welding or fusion alone which prevents any relevant movement of the wires with respect to one another. Therefore also any onset of an unraveling of the fabric structure of the occluder is prevented. These are the prerequisites for the further handling. Without this fusion or welding of the proximal end portion of the wire bundle to the NiTinol sleeve, the wires could not withstand the tensile forces, which occur during the handling or use of the occluder, without an unraveling of the wire mesh of the occluder. If the microplasma welding of the end portion of the wire bundle to the NiTinol sleeve were omitted, a straightforward frictional action of the end portions of the wires on the inside of the NiTinol sleeve cannot fixate theses end portions firmly to the effect that an unraveling prevention of the fabric structure and a reliable fixation by and of an unraveling providing element can be provided.

The NiTinol sleeve is therefore not suitable, alone, for fixing the wire ends in such a way that an unraveling of the wire fabric during the customary handling of the occluder is prevented. Instead, the NiTinol sleeve could even be omitted and a fixing of the wire ends could take place solely by these wire ends being welded or fused to one another e.g. in a jig as described below. The use of a NiTinol sleeve has essentially the purpose of fastening an external element, such as a steel sleeve with an engagement surface for a delivery device, e.g. an internal thread, to it or at it. In this manner it is made possible to attach a delivery device to the medical implantable device, e.g. to screw in a guide wire for the occluder. For this purpose, local deformations are generated on the inside of the steel sleeve by laser technology and serve for fixing the steel sleeve on the NiTinol sleeve. The guide wire is subsequently screwed into the internal thread of the steel sleeve. The NiTinol sleeve has a defined extension, e.g. a well defined outer diameter and inner diameter. The inner diameter is chosen, such that the sleeve easily slides over the wire bundle, without any clamping action. A clamping action would hinder the sleeve from sliding along the wire bundle, as is desired. The sleeve has to be threaded on the wire bundle over its end. Then the sleeve is slid along the wire bundle towards a position where it will be welded to the wire bundle after cutting thereof.

Figure 3:
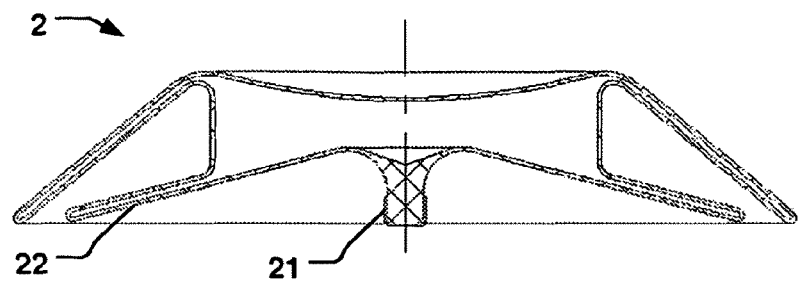
FIG. 3 shows a schematic sectional illustration of an occlusion instrument with cut-off wire ends.

In addition it may be mentioned that a clamping would restrict the individual wires from moving relative each other. This is highly desired during a heat forming process, where e.g. a sock or funnel shaped wire mesh (explained below) is brought to a desired form. The desired form may be a dumbbell, bell, pear shape, etc. Therefore, the welding and fixation of the individual strands towards each other is performed after the medical implant has obtained its shape. The wire bundle is merely protruding as a parallel bundle of strands. The strands are not fraying, as e.g. is shown in FIG. 2a or FIG. 3.

An additional or alternative method is to weld the NiTinol strands in a jig or template form. The jig is beneficial in respect of constraining the bundles end while welding giving the welded NiTinol clot a well defined dimension, e.g. a circumferential dimension. In this case the well defined dimensions of the NiTinol sleeve mentioned above are not needed, they are instead provided by the jig. The welding clot itself has then well defined dimensions implied by a mould structure of the jig. These well defined dimensions allow precise fitting of another element to the cut bundle end. For instance another element, such as a connection sleeve may be slid over the bundle end of well defined dimensions. In addition, a jig may give the welding clot desired outer contours or shapes, as described below.

A result with a distended welded clot could hence be avoided. Additional positive outcomes for using a jig are collecting the NiTinol wires to a bundle prior to administrate the welding and that the jig can be designed with protrudes, ridges, groves, threads, markings or any other physical deformations. The mold of the jig may also in addition or alternatively have an asymmetric shape in rotational direction. In addition, or alternatively, the asymmetric shape of the jig is an asymmetric shape in longitudinal direction of the mold. As the jig is preferably made of a material non-compatible with the material of the wire bundle, e.g. NiTinol, a mirror images of the protrudes are transferred from the jig to the NiTinol clot. Non-compatibility is e.g. given due to substantially different melting points of the two materials of the jig and the wires.

The defined proportions and dimensions of the bundle are thus provided by an internal mould surface of the template jig, and providing the connection interface by an external surface of the weld when having set.

Alternatively, a sleeve, as mentioned above, may be provided with an asymmetrical shape around the bundle of strands.

In addition the sleeve may comprise the abovementioned physical deformations for an improved connection interface.

Thus the defined proportions and dimensions of the bundle are provided by an internal surface of the sleeve, and providing the connection interface is provided at least partly by an external surface of the sleeve.

The steps stated above for fixing the wire ends, thus provide a well defined connection interface devised for fastening an element, e.g. the steel sleeve with an internal thread or other delivery interface, to the proximal end of the medical device are described in more detail below.

In more detail, a method of producing a medical implantable device that comprises a bundle of strands is described. The method comprises holding the bundle of strands in a desired shape with a holding unit, e.g. a jig, or a sleeve. Subsequently the bundle of wires is cut while the bundle is held within the holding unit. Thus a cut end of the bundle of wires is created. Then the bundle of strands is welded together at the cut end while keeping the holding unit arranged at the cut end. A sleeve may be made of the same material as the strands and at least partly be melt to the cut end. Thereby a welded end of the bundle of strands is created that has defined proportions and dimensions given by the holding unit, or at least partly by the holding unit. Thereby a connection interface is provided at the welded end devised for fastening an external element to the welded end.

A connection is formed between the external element and the connection interface, thus facilitating assembly of the two components to each other. In an embodiment the connection between the external element and the connection interface is a fixed or temporary non-positive form fit connection.

The strands and the external element are preferably composed of two different materials which have a substantial different melting point, wherein the strands and the external element cannot be welded to one another.

When the holding unit is a sleeve, the method comprises sliding the sleeve over the bundle of strands of the medical implantable device for holding the bundle.

The parallel bundle of mesh ends 20 of a blank of an occlusion instrument 2 are held in a thin-walled sleeve 21 in such a way that they approximately fill its cavity. The sleeve is arranged to be a holder, but not adapted to clamp. The sleeve 21 is fixed at a specific distance from the proximal retention disc 22, for example, by means of a jig. However, the sleeve does not provide (used to) any clamping action on the bundle of strands contained therein.

See FIG. 2a—Step 100

Produce medical implant of wire strands. This is not further described herein, wherein reference may be made to e.g. DE 10 338 702. Reference is made to FIGS. 8a, 8b, 9 and 10.

A holder unit is positioned around a bundle of strands 20. The holder unit is e.g. a sleeve 21 or a jig 25.

Figure 2C:
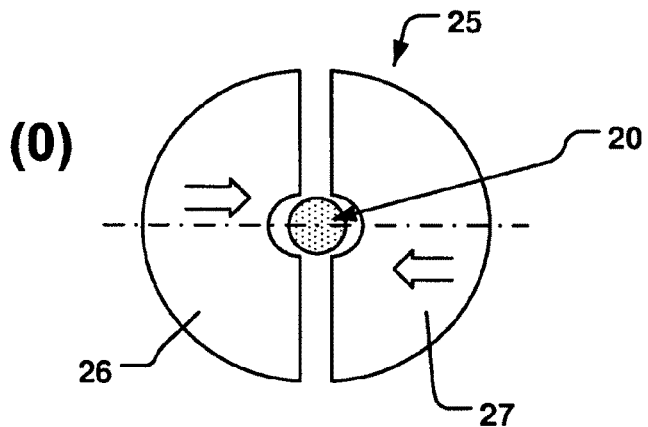
Figure 2C:
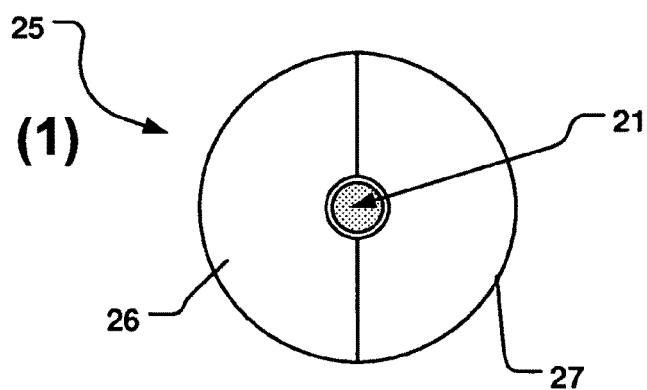
Figure 2D:
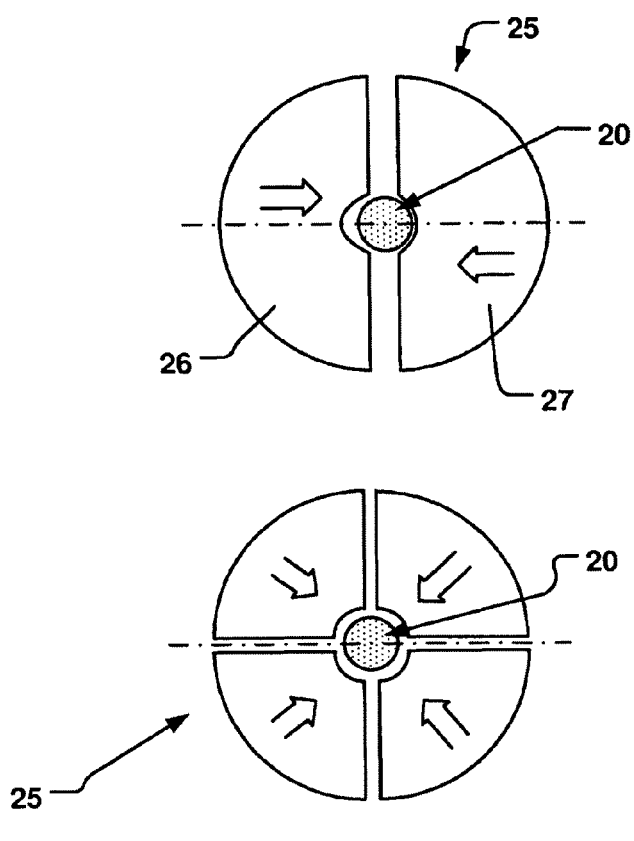
FIG. 2d cross sectional views of variations of the template-like jig.

FIGS. 2a, 2b and 2c show schematic sectional illustrations of an occlusion instrument with an axially aligned bundle of wire ends. FIG. 2d is a cross sectional view of variations of the template-like jig. The template jig 25 may be made of two or more sections that are devised to be assembled to each other around the bundle of wires with its mould portion.

The template may provide a desired shape to the bundle of wires prior to Microplasma welding, by means of its internal mould portion. In this manner, the bundle has a defined shape according to the template shape after the Microplasma welding is finished. This may be used for e.g. bayonet fittings. Connection interfaces are provided. For instance a hexagonal form may be one of many advantageous forms, e.g. for rotational torque transmission.

Alternatively, or in addition, asymmetric shapes may be given to the bundle. Asymmetric shapes of the bundle may advantageously provide a defined orientation of the medical implant. The asymmetrical shape may be detected on patient image data provided during implantation of the medical implant. The asymmetrical shape may also be used for identification via a connected delivery device and the orientation thereof. With a known orientation of the delivery device and a known relation of the delivery device to the medical implant, when attached to each other, the orientation of the medical implant is known.

This may further be improved, when components with different radiopacity are attached to each other. This facilitates for identifying an orientation of the medical implant, e.g. in relation to a delivery adapter or a delivery device attached to the medical implant. For instance the medical implant may be of a radiopaque shape memory polymer (SMP) and a delivery adapter attached to a bundle of strands of the medical device may be made of metal or another material being more radiopaque than the SMP material. In this case a contrast between the two components is identifiable. Also, one of the components may be non-radiopaque. In any case a difference in radiopacity of the two components provides an enhanced contrast and contributes to advantageous orientation identification of the medical implantable device and the external element attached to it.

Rotational transmission of torque may advantageously be provideable by such embodiments comprising protrusions or an asymmetric shape. This facilitates delivery of the device as precise positioning of the medical implant is provided correctly.

Welding

1. First Laser welding—Step 110:

The projecting proximal wire ends are cut off, approximately flush with the sleeve 21 or jig, by means of a laser beam. Thus a cut end of the medical implantable device 2 is produced, See FIG. 2b (jig) or FIG. 3 (sleeve).

2. Second Laser Welding—Step 120

By means of a laser, unevenness is smoothed out by fusion and the sleeve 21 and/or cut bundle end is brought to a predetermined length dimension, so that defined welding conditions are present for the subsequent microplasma welding.

3. Microplasma Welding—Step 130:

By means of a plasma arc, the NiTinol wires 41 are fused with the NiTinol sleeve 21 over a defined length. This gives rise to a flattened hemisphere 40 which has on the circumference a slightly bulged elevation 45 with respect to the sleeve 21. The distal end edge 49 of the sleeve 21 extends radially over the bundle 41. In case the entire sleeve 41 is melt during welding, a bulge is defined.

Alternatively, the jig 25 provides a defined proportion and dimension of an internal mould portion for welding the bundle end together. In the case of a template-like jig 25, a fused welded clot of defined dimension is created in the mould portion of the template-like jig.

Figure 4A:
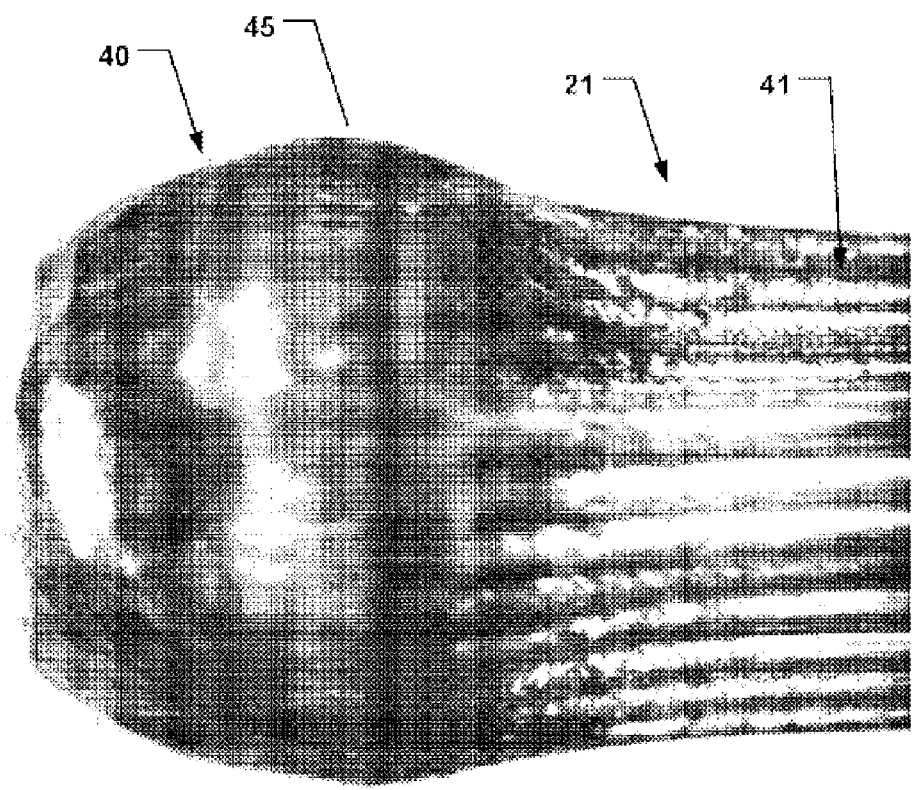
FIG. 4a shows an illustration of a proximal end, welded by means of microplasma, of a wire mesh without a sleeve.
Figure 4B:
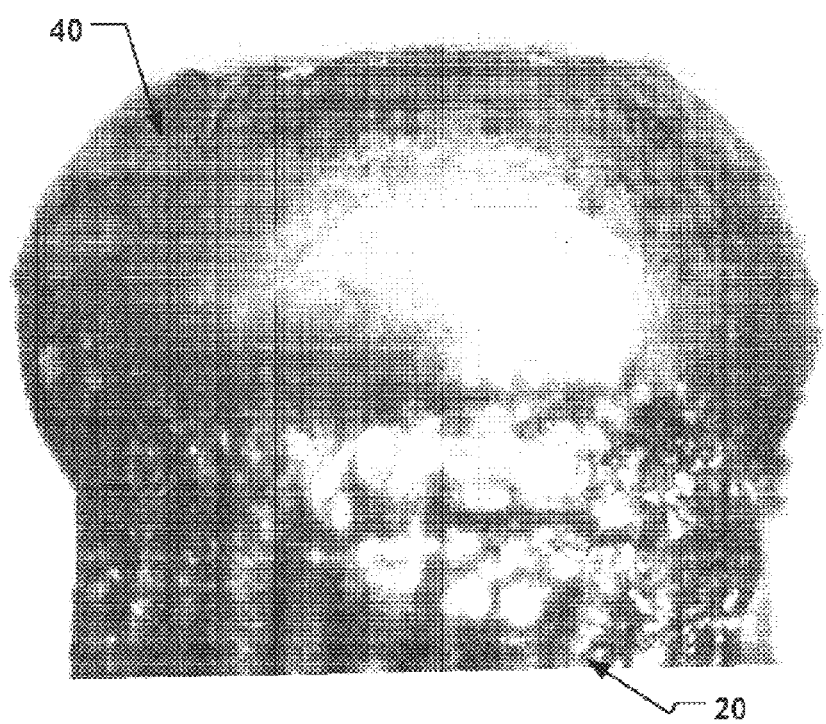
FIG. 4b shows a further example of a proximal end of wire meshes, welded by means of microplasma.

In the case of a weld without a sleeve, a bulge may be produced by the jig, as shown in FIG. 4a and FIG. 4b. FIG. 4a shows an illustration of a proximal end, welded by means of microplasma, of a wire mesh without a sleeve. FIG. 4b shows a further example of a proximal end of wire meshes, welded by means of Microplasma, having a smaller protruding extension over the diameter of the bundle of strands 20, and a slightly asymmetric shape.

Figure 4C:
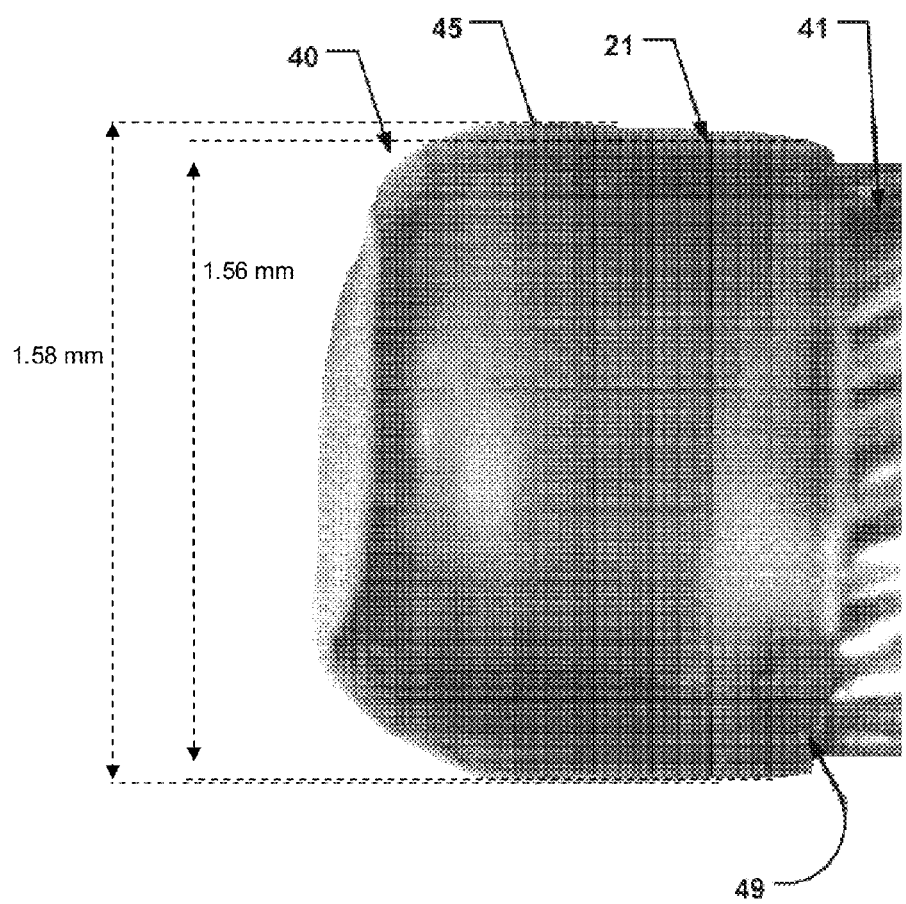
FIG. 4c shows a further example of a proximal end of wire meshes, having a sleeve and being welded by means of microplasma.

FIG. 4c shows a further example of a proximal end of wire meshes, having a sleeve and being welded by means of Microplasma. In FIG. 4c elevation of the bulge of a metal clot over the circumference of a sleeve are illustrated. In a nonlimiting example the sleeve has an outside diameter of 1.56 mm and the bulged elevation of the hemisphere 40 has a diameter of 1.58 mm, that is to say a height of the elevation of 0.1 mm over the entire circumference of the sleeve 21. This indicates that embodiments of the medical implants are worked with very high precision at small dimensions.

The effect of the Microplasma welding and the time of application of the plasma arc is adjusted accordingly. For instance a sleeve may be complete melted with the strands situated therein. In this case, after this microplasma welding step, the sleeve can no longer be identified in the welding clot. The welding clot is uniformly in this case.

By providing the holding unit, manufacturing is made faster and cheaper. Laser energy of higher power is used than merely melting the end. Melting without the holder unit at identical laser powers results in an undefined shape of the weld, unsuitable for mass production. Applicants have found that the laser power can be increased to approx. three times the power. In this manner, welding is made faster. Manufacturing becomes cheaper not only to the faster welding process, but also thanks to the fact that a well defined connection interface is created with high precision. This facilitates continued assembly of an external element to the welded end of the medical device.

4. Third Laser Welding—Step 140:

When using a jig 25, this is removed by taking apart the parts thereof. As the jig is made of a material having a different higher melting point than the bundle of wires (or now the melted clot), it is easily removed as it does not attach. The flattened hemisphere (with sleeve) or the proximal end of the bulge (jig) obtained by means of the plasma arc is optionally shortened to the desired length dimension in a subsequent work step by means of laser pulses. Likewise, the holder is brought to the required diameter at the bulged marginal zone, if the oversize is too great, by stripping away of material.

The melt in the core and the bulged elevation of the marginal zone are essential constituents of the connection between the bundle of the mesh, the sleeve (if used) and external element (coupling) in the case of embodiments with non-positive connection.

5. Fourth Laser Welding—Spot Welding—step 150:

The external element, here a coupling 50, comprising a delivery internal thread 51, is pushed, in a similar way to a sleeve, over the bulged elevation and the sleeve 21, oriented, for example, in a jig and fixed with respect to the proximal end of the welded wire bundle.

Figure 5D:
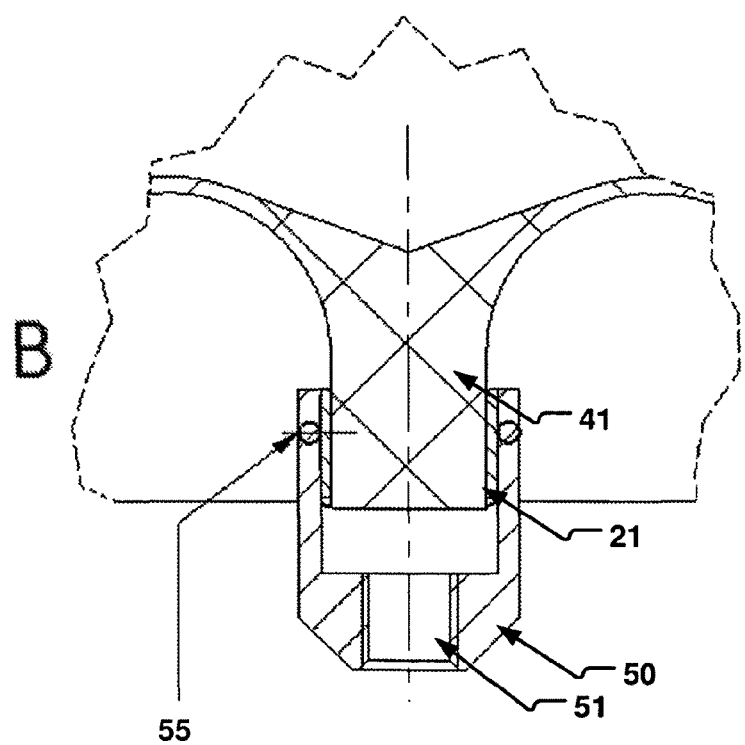
FIG. 5d shows a schematic sectional view of a coupling with internal thread pushed over a sleeve in accordance with a further embodiment.
Figure 5A:
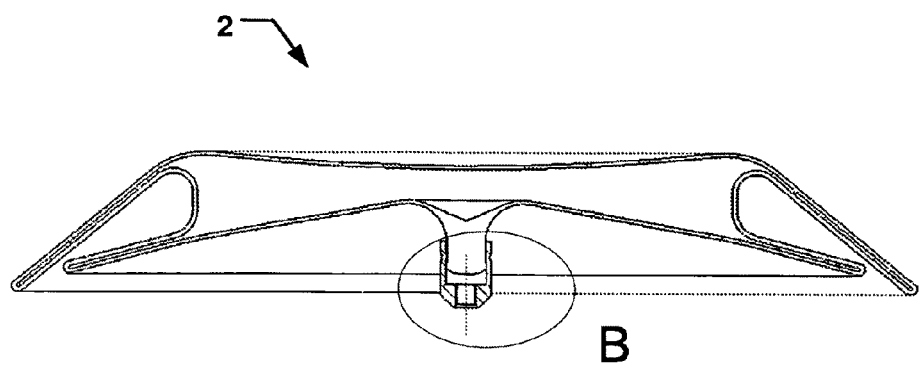
FIG. 5a and FIG. 5b show a schematic sectional illustration of a coupling with an internal thread pushed over a bulged elevation and a sleeve.
Figure 5B:
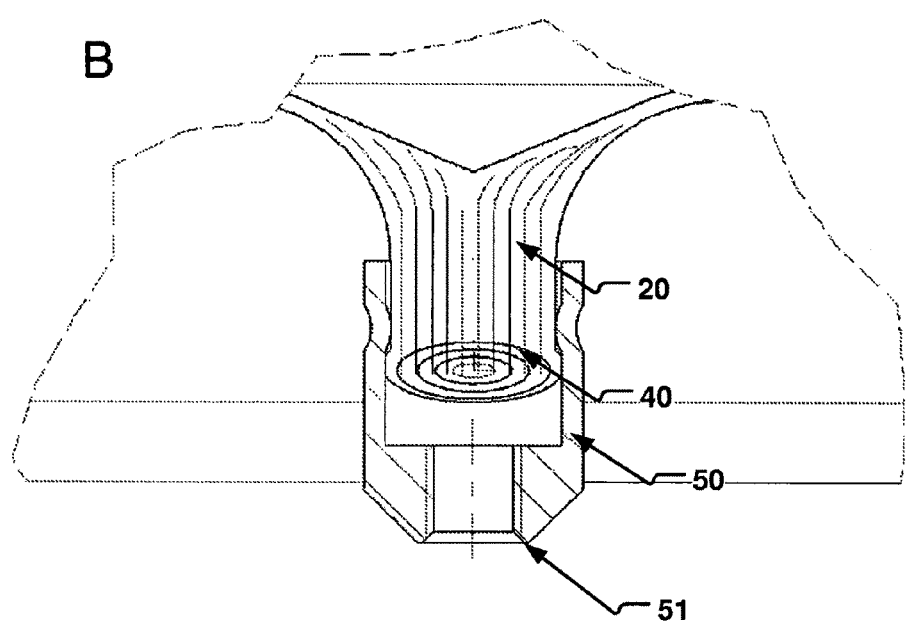

See FIG. 5*a* and the enlarged illustration of the region B in FIG. 5*b*. The coupling 50 has a reduced internal diameter as shown in FIG. 5*b* which is formed after sliding the coupling over the clot 40 with a distal opening thereof.

Figure 5C:
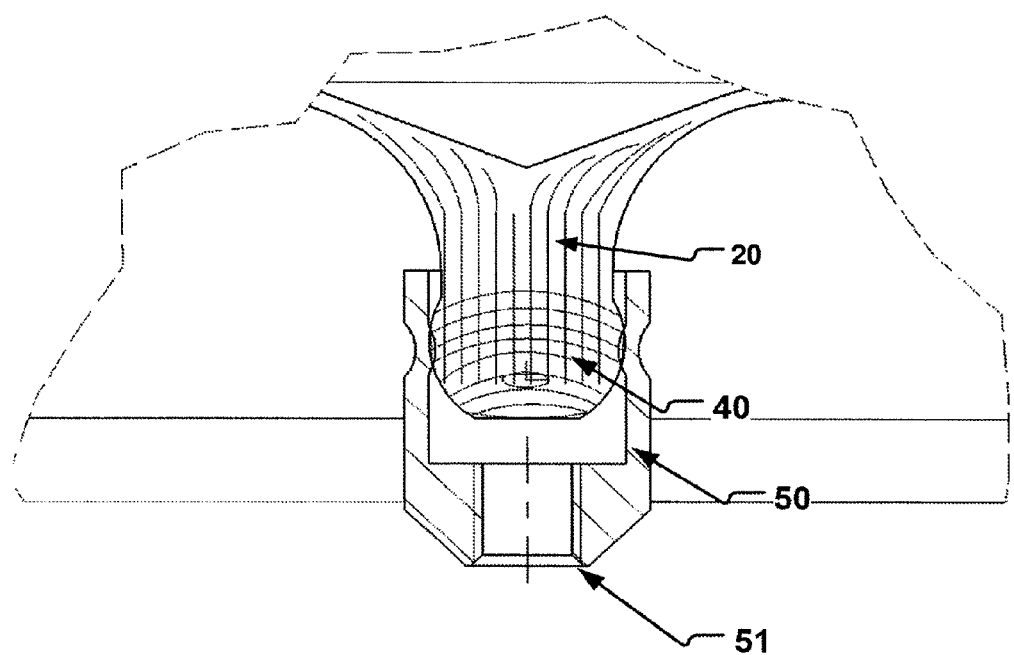
FIG. 5c shows a schematic sectional view of a coupling with internal thread pushed over a bulged elevation in accordance with a further embodiment.

In FIG. 5*c* a further example is illustrated, whereby the attachment takes place directly on the welding clot 40. In this embodiment the interior of the steel sleeve is deformed onto the welded clot. This is a more reliable attachment than clamping to a bundle of wires which are inherently movable.

Figures 6, 7A:
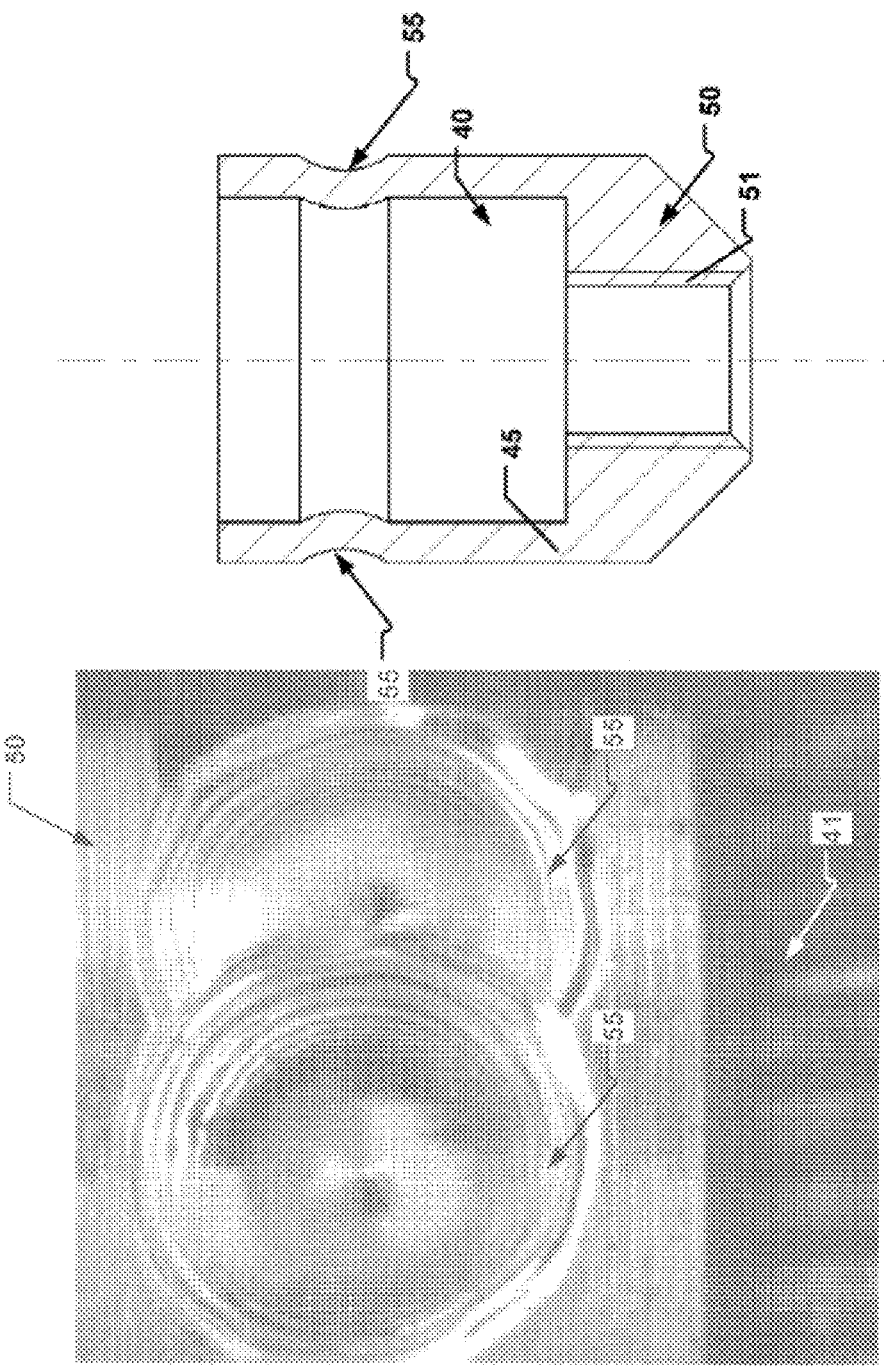
FIG. 6 shows a schematic illustration of weld spots in a caterpillar arrangement on a coupling.
FIG. 7a shows a schematic sectional illustration of a contraction of a coupling.
Figure 7B:
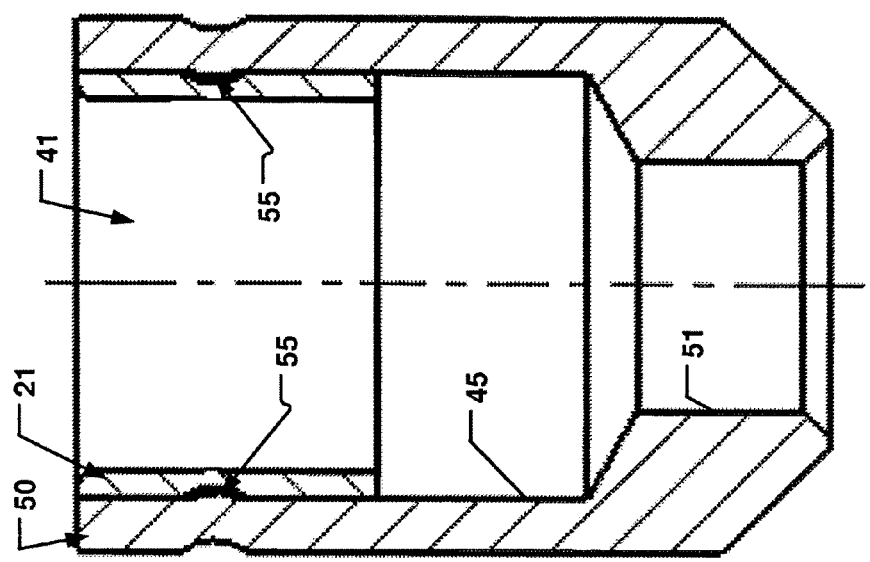
FIG. 7b shows a schematic sectional illustration of a coupling affixed to a sleeve.
Figure 11:
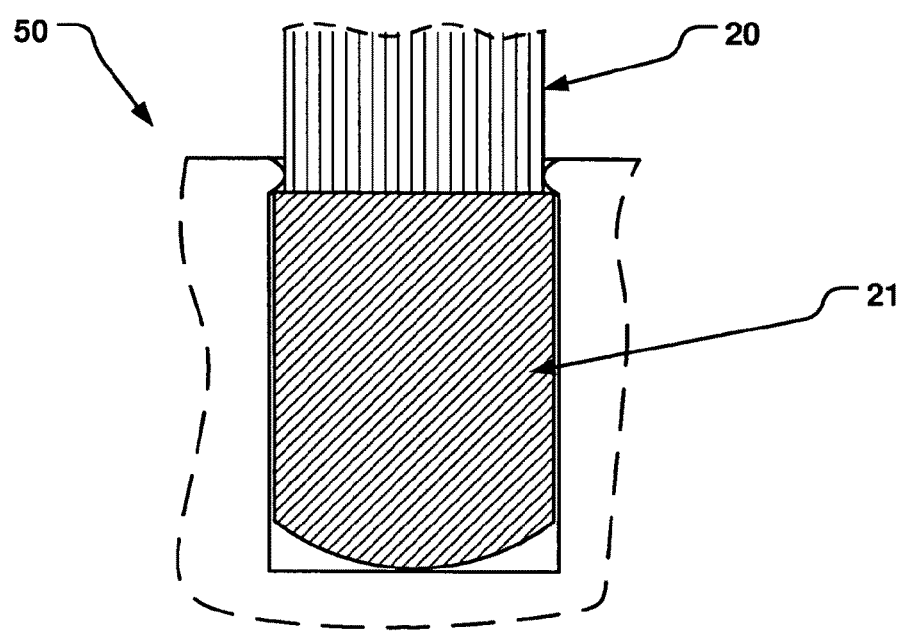
FIG. 11 shows a schematic illustration of the fused bundle clot inserted in the coupling.

Producing the reduced internal diameter is e.g. made by weld spots 55 that are applied radially by means of a laser beam in a caterpillar like arrangement (see FIG. 6). An annular contraction of the coupling 50 in the form of a cuff is obtained, which is connected non-positively to the sleeve 21 when the contraction is made distally of the weld bulge (FIG. 5*a* or 5*c* or FIG. 11). The connection is a positive connection in the case of having the contraction at the bulge (FIG. 5*c*, 5*d*). Furthermore, an additional positive connection with the weld or the sleeve 21 may be obtained. Alternatively a form fit is provided in some embodiments. For instance an embodiment may be provided, see e.g. FIG. 11.

The weld spots 55 are made contactless and are to be understood as spots or local deformations. No melting or welding of the two elements to each other is performed. The deformation of the outer element may be made in such a manner that it does not at all interfere with the inner element, see e.g. FIG. 11.

An example of a caterpillar like weld bead on the outside of the coupling 50 is shown in FIG. 6.

The contraction of the coupling 50 in accordance with FIG. 5*b* is illustrated in a diagrammatic sectional drawing in FIGS. 5*b*, 5*c*, 5*d*, 7*a*, 7*b*, and 11 in different embodiments respectively.

Figure 8A:
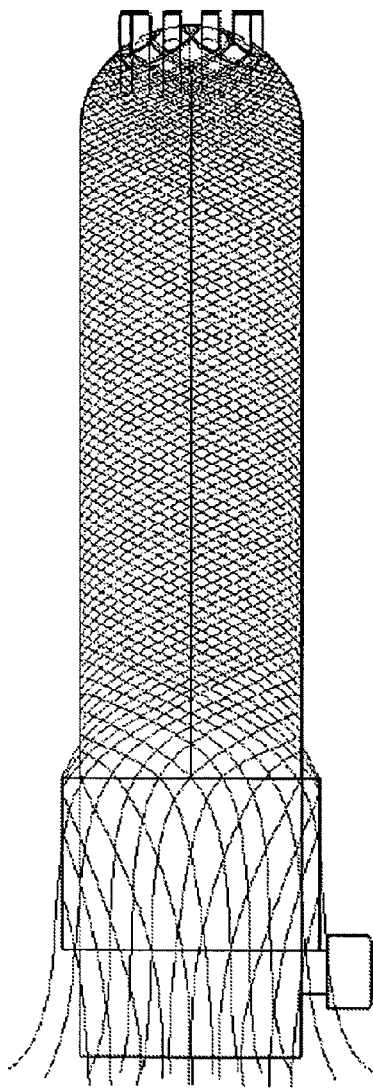
FIG. 8a shows a schematic illustration of a mesh stocking with a spherical head resulting in a braided sock fabric.
Figure 8B:
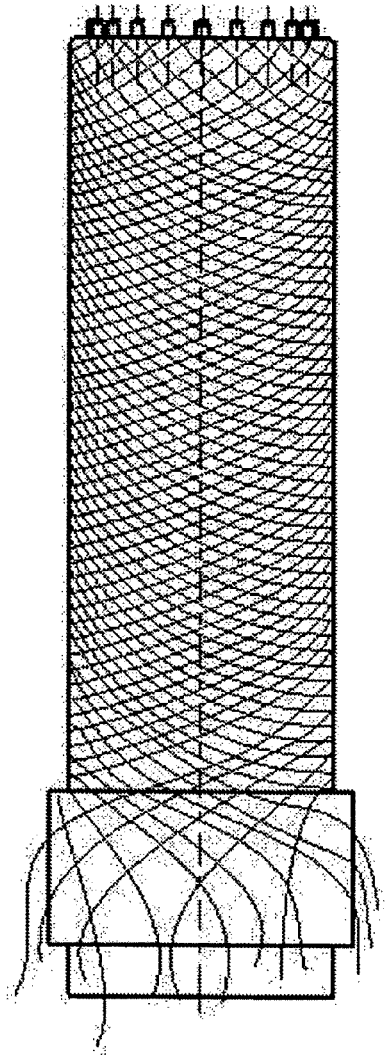
FIG. 8b shows a schematically illustration of a mesh stocking for a braided funnel mesh.

FIG. 8*a* shows a braided mesh sock for producing a medical device having a bundle of wires at an end. FIG. 8*b* shows a mesh sock for a funnel braiding for producing a medical device having a bundle of wires at an end.

In embodiments, neither the NiTinol sleeve nor the steel sleeve with an internal thread constitute a clamp which is suitable for firmly clamping the wire ends of the strands or of the occluder, in order to prevent an unraveling of the wire fabric.

Monofilament wires are used as "strands", the fraying of the ends of such strands is not possible, since a monofilament wire cannot fray at its ends.

Unraveling is avoided by welding of the strands together. However, this preventing of unraveling may not be needed at all, e.g. after a heat forming process, where no unraveling occurs, see e.g. FIG. 10.

Figure 9:
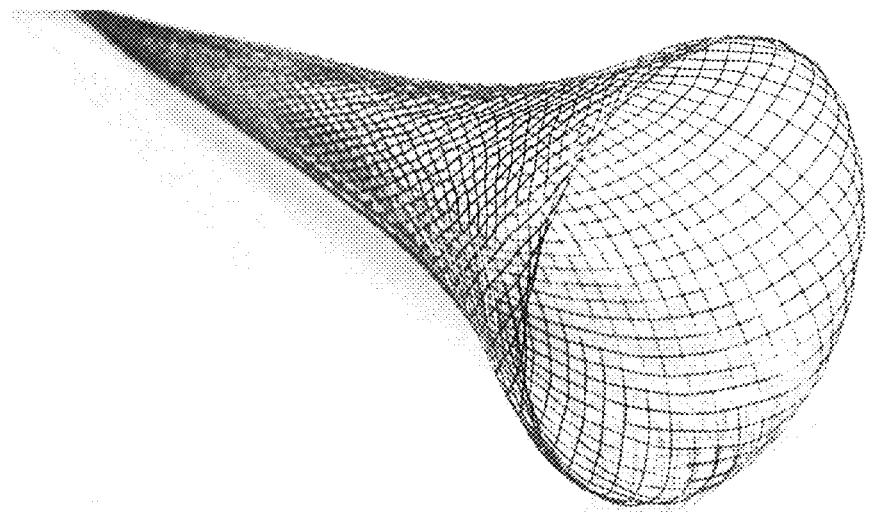
FIG. 9 shows a schematic illustration of an occluder blank in the form of a wire fabric for a funnel occluder.

FIG. 9 shows an occluder blank in the form of a wire fabric for a funnel occluder.

Clamping or welding may in some instances also be undesired. For instance, in case the strands need to be movable relative each other during a manufacturing process and can therefore only be affixed relative each other at the end or a later stage of the manufacturing process. This may for instance be the case when forming a dumbbell shaped occlusion device from a tubular sock braiding. When giving the sock braiding a desired dumbbell shape, the strands of a bundled end section thereof have to be movable relative each other. Otherwise the product will have inherent tension and loose its advantageous flexibility properties. After a heat setting forming procedure of the dumbbell shape, or the like, the bundle does not need to be clamped or welded. However, a sleeve may be affixed to the bundle as explained hereinafter. Alternatively, or in addition, a template may be arranged around the bundle in order to give it a desired shape.

Figure 10:
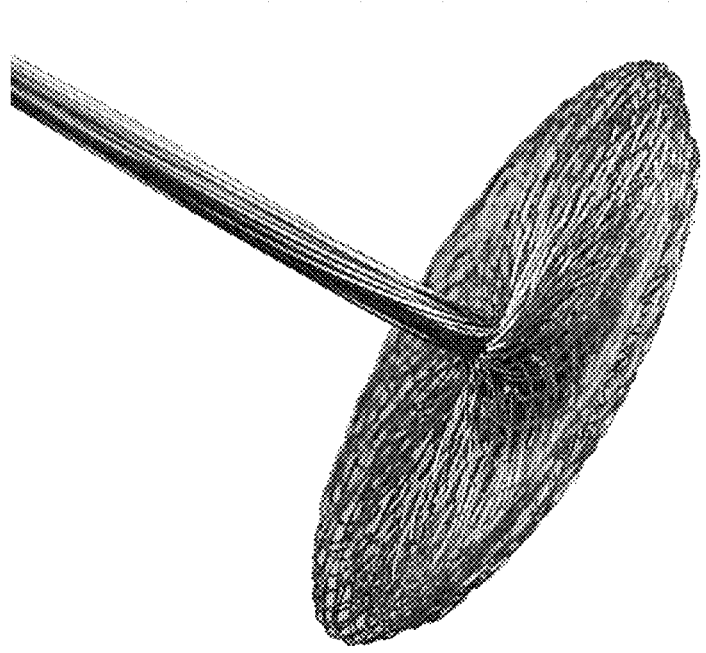
FIG. 10 shows a schematic illustration of the occluder blank of FIG. 9 after heat treatment and shaping.

FIG. 10 shows the occluder blank of FIG. 9 after heat treatment and shaping. It can be seen that the projecting wire ends do not fray and the mesh does not unravel, since the elongate wire ends (running to top left in the figure) run, stress-free, out of the shaped wire mesh. A clamp for holding the wire ends together is not necessary per se.

The medical implantable device is for instance a self-expandable occlusion instrument, for example for closing an ASD or PFO in a septum of an atrium, or for closing a VSD in a ventricle. The device comprises a mesh of thin wires or strands 200, which acquires a suitable shape by means of a shaping, forming and/or heat treatment method. The occlusion instrument has a front-side proximal retention region 22 and a rear-side distal retention region 220, and the ends of the wires or threads converging in the proximal retention region. Furthermore, the occlusion instrument has a middle region 210 between the proximal and the distal retention region. The occlusion instrument is in this case designed such that, in a collapsed or compressed state, it can be introduced by means of a catheter into a patient's body with minimal invasiveness and can be positioned in the patient's body.

Such medical implantable device are for instance generally described in US20070043391A1, US20070112380A1 or US20070112381A1 (of the same applicant as this application—these are hereby incorporated by reference in their entirety).

Thus, for example, to produce an occluder, such as described in US20070043391A1, US20070112380A1 or US20070112381A1, the above mentioned method may be used to improve the devices further. Thanks to the connection method illustrated in the present description there is no need at all for a clamp for firmly clamping the strand ends or the occluder ends. In the occluder, the arranging of the strand ends for connection of a delivery element is brought about solely by the welding of the proximal end of the axially extending bundle of strands. In this case, it is noted that, in this and other embodiments, the strands preferably consist of monofilament NiTinol wires.

In some medical implantable devices, the bundle of strands may have en inherent tension tending to unravel the bundle and the fabric of the medical implantable device. For these devices, the welding of the end prevents to avoid unraveling of the fabric structure. Such devices are e.g. made of tubular braided fabrics, wherein one or two ends of the tubular braid are compressed and need to be fixated. However, the present method is also useful with bundles of wires that have no inherent radial tension.

When the external element, such as a delivery adapter is put in place and connected to the wire bundle, a bore or other recess can also be made transversely to the longitudinal direction, in order, alternatively or additionally to the threaded fastening, for example of a catheter, to allow fastening with the aid of a gripper or other auxiliary device or wire. The gripper may latch releasably, for example, into the bore orifice, the bore here not needing to run through the entire diameter of the sleeve. An auxiliary wire may be led as a loop through a bore. For example, an operating implement for an implantation intervention is described in WO07054118A1 (of the same applicant as this application—this is hereby incorporated by reference in its entirety). Consequently, such sleeves or cuffs can be gripped reliably and, to check the seating of the occlusion instrument, also released from the operating implement again—even the renewed gripping of the occlusion instrument, for example in order to change its seating or for immediate explanting, is readily possible.

Some embodiments make use of a form-grip method to secure delivery of the occlusion instrument. The exterior of the welded bundle end is highly defined in respect of its physical dimensions according to the above described manufacturing procedures. A benefit of this is the possibility to slide an exterior introduction coupling outside over this defined bundle end. No tools or manual compression is required. The exterior introduction coupling may comprise bulges on the interior distal to the bottom of the same, see FIG. 11. These bulges could be at least one annular bulge on the inside of exterior introduction coupling at a distance from the interior bottom of the same that is slightly larger than the height of an appropriate sleeve. These bulges are radially oriented towards the longitudinal axis of the exterior introduction coupling and have dimension to affix the occlusion instrument upon delivery thereof.

As the exterior introduction coupling is pushed on to the sleeve the bulges are compressed by means of dimensional aspects to a semi-tight fit. When the sleeve and the exterior introduction implement coupling is fully engaged, i.e. the sleeve is securely positioned, the compression force of the bulges ends as the bulges are positioned with a slightly larger distance from the interior bottom of the exterior introduction implement coupling than the sleeve axial dimension when placed in the exterior introduction implement coupling.

Further developments to ensure administration of the occlusion instrument, welded according to process description, is that protrusions, ridges, threads grooves and other physical distinct markings in the template-like jig are incorporated to the melt. The mould part of the jig should for these embodiments is designed with either positive or negative marks (protrusions or recesses) to the desired correspondingly mating appearance of the finished melt of the bundle end. Possible protrusions or recesses on the melt become set in the jog mould comprises longitudinally extending axial ridges, and/or annular ridges, and/or partly annular ridges, aligned with the longitudinal axis of the occlusion instrument. These markings may have incorporated distinct corners or directional shape changes providing a locking capability. An exterior introduction implement coupling may in some embodiment be designed to lock-on to the occlusion instrument by means of matching protrusions, bulges or groves, e.g. similar to or like a bayonet fitting. Some additional embodiments may further comprise a detachable exterior introduction implement coupling from the occlusion instrument. This may be beneficial in respect to minimize weight of the medical device as un-necessary structures is detached and thus no longer incorporated with the deployed medical device. A further positive aspect is that the occlusion instrument will have no projecting introduction implement coupling. For instance, in case the bundle of strands is positioned in the centre of the proximal retention area, a more smooth surface will be present.

The exterior introduction implement coupling is for some embodiments fixed to the introduction wire or the introduction implement by means of a threaded intersection. By unbolting the occlusion instrument from the introduction wire or the introduction implement the occlusion instrument will be released and may be detached from the occlusion instrument. For other embodiments the exterior introduction implement coupling is firmly fixed to the introduction wire or the introduction implement. Release of the occlusion instrument is performed by means of a connection interface adapted to provide a releasable connection between the occlusion instrument and exterior introduction implement coupling. The introduction wire or the introduction implement is manipulated in order to un-lock the occlusion instrument.

In some embodiments the means of manipulation uses a interior pusher by which a counter force may be administrate to facilitating release.

The method may also be carried out with other medical implants than occluders.

The sleeve provided with a thread may also comprise other embodiments, such as, for example, proximal spherical heads.

Even different materials may be used, such as, for example, polymer materials, or X ray opaque polymer materials, as described, for example, in U.S. application 60/940 607 (the same applicant as this application—this is hereby incorporated in full by reference).

Visibility in X-ray may be improved by attaching components with different radiopacity to each other as described herein.

A force fit or form fit, as described above for different embodiments, may also provided between two components of the same or similar material, wherein welding is not needed, avoided, prevented or refrained from by the embodiments. This may for instance be the case in sensitive production environments where e.g. risk for explosion is present.

A person skilled in the art would be able to comprehend that obvious modifications to the examples described are possible, without departing from the scope of the accompanying claims.

What is claimed is:

1. An implantable medical device comprising a bundle of strands, said device comprising a welded end portion configured as a connection interface and an external element coupled to said connection interface in a non-clamped manner, and wherein:
   said welded end portion has defined proportions and dimensions,
   said connection interface comprises a sleeve positioned around said bundle of strands at said welded end portion,
   said sleeve is made of the same material as said bundle of strands at said end portion,
   said sleeve is at least partly fused to said welded end portion, and
   said external element is coupled to said connection interface outside and over said welded end.

2. The medical implantable device according to claim 1, wherein said external element is fastened to said connection interface in a permanent, non-positive connection.

3. The medical implantable device according to claim 1, wherein said external element is fastened to said connection interface in a temporary, releasable connection.

4. The medical implantable device according to claim 1, wherein said external element is a delivery adapter.

5. The medical implantable device according to claim 4, wherein said delivery adapter is a steel sleeve non-positively fit to said connection interface, and wherein said strands are made of a nickel titanium alloy.

6. The medical implantable device according to claim 5, wherein said steel sleeve comprises an engagement surface for a delivery device.

7. The medical implantable device according to claim 6, wherein said engagement surface is a threaded surface.

8. The medical implantable device according to claim 1, wherein said strands and said external element are of different materials.

9. The medical implantable device according to claim 8, wherein said different materials have different radiopacity.

10. The medical implantable device according to claim 1, wherein said connection interface is asymmetric in rotational direction of said bundle.

11. The medical implantable device according to claim 1, wherein said connection interface is asymmetric in longitudinal direction of said bundle.

12. The medical implantable device according to claim 1, wherein said connection interface comprises at least one protrusion and/or recess.

13. The device of claim 1, wherein at least a portion of said connection interface is provided by an external surface of said sleeve.

14. The device of claim 13, wherein said external surface of said sleeve has an outer diameter that provides a defined dimension of the welded end portion.

15. The device of claim 1, wherein said bundle of strands and said sleeve are made of a metal.

* * * * *